United States Patent [19]

Auer

[11] Patent Number: 4,981,580

[45] Date of Patent: Jan. 1, 1991

[54] COINCIDENCE ARBITRATION IN A FLOW CYTOMERY SORTING SYSTEM

[75] Inventor: Robert E. Auer, Miami, Fla.

[73] Assignee: Coulter Corporation, Hialeah, Fla.

[21] Appl. No.: 345,975

[22] Filed: May 1, 1989

[51] Int. Cl.$^5$ .............................................. B07C 5/342
[52] U.S. Cl. ...................... 209/3.1; 209/564; 209/579; 209/906; 356/39; 364/413.08
[58] Field of Search ................. 209/3.1, 3.2, 552, 559, 209/564, 565, 906, 579; 356/39, 72, 335, 338; 364/413.08; 250/222.2, 214; 361/226; 324/71 A

[56] References Cited

U.S. PATENT DOCUMENTS

| | | | |
|---|---|---|---|
| 3,380,584 | 4/1968 | Fulwyler | 209/3 |
| 3,675,768 | 7/1972 | Legorreta-Sanchez | 209/3.1 X |
| 3,826,364 | 7/1974 | Bonner et al. | 209/3.1 |
| 3,963,606 | 6/1976 | Hogg | 209/3 |
| 4,148,718 | 4/1979 | Fulwyler | 209/906 X |
| 4,230,558 | 10/1980 | Fulwyler | 209/3.1 |
| 4,447,883 | 5/1984 | Farrell et al. | 324/71.4 X |
| 4,487,320 | 12/1984 | Auer | 209/3.1 |
| 4,510,438 | 9/1985 | Auer | 356/72 X |
| 4,667,830 | 5/1987 | Nozaki et al. | 209/3.1 |
| 4,778,593 | 10/1988 | Yamashita et al. | 209/3.1 |

Primary Examiner—Donald T. Hajec
Attorney, Agent, or Firm—Harry W. Barron

[57] ABSTRACT

A coincidence arbitration system for a sorting cytometer which detects and sorts particles using a flow chamber and a stream of droplets. Those droplets containing selected particles are sorted by selectively applying a charge thereto and passing the droplets through deflection plates. After detection, the particle data is delayed and analyzed to make sort decisions. The delay is for a period of one and one fourth droplet time periods less than the time the particle is formed into a droplet. At the time the command is issued creating the charge on the droplet to be formed, the coincidence arbitration circuit looks four quarter droplet times ahead and behind of the event to determine whether a coincidence is occurring, and if so, whether the coincidence is with a similar type of particle or a different type of particle. Based on this information, appropriated sort or no-sort commands are issued.

45 Claims, 4 Drawing Sheets

COINCIDENCE ARBITRATION IN A FLOW CYTOMERY SORTING SYSTEM

This invention relates to a flow cytometry sorting system in which various types of particles, such as blood cells, are sorted into various containers, and more particularly, to such a system including coincidence arbitration means for reducing the instances of aborted sort commands as a result of particles being detected too close to one another to be individually sorted.

BACKGROUND OF THE INVENTION

In the past it has been suggested that particles, such as blood cells, may be detected and separated using a device known as a flow cytometer. The fluorescent dye treated cells are injected into a narrow jet stream surrounded by an electrically conductive sheath of fluid. Light, such as from a laser beam, is directed at the passing particles and various parameters, such as front and side light scatter and various fluorescent wavelengths of light may be detected to identify the cell. As the jet stream of fluid containing the cells exits the flow chamber, a mechanism, such as an ultrasonic or acoustic wave generator, cause the stream to be broken into a series of individual droplets. The detected cells will then be entrapped within one droplet and the individual droplets may be sorted into different containers to obtain a sample of desired cells.

DESCRIPTION OF THE PRIOR ART

Examples of sorting flow cytometers, such as described in the preceding paragraph, are shown in U.S. Pat. No. 3,380,584 in the name of M. J. Fulwyler, entitled "Particle Separator"; U.S. Pat. No. 3,826,364 in the name William A. Bonner et al, entitled "Particle Sorting Method And Appartus"; U.S. Pat. No. 3,963,606 in the name of Walter R. Hogg, entitled "Semi-Automatic Adjustable Delay For An Electronic Particle Separator"; U.S. Pat. No. 4,148,718 in the name of M. J. Fulwyler, entitled "Single Drop Separator"; U.S. Pat. No. 4,230,558 in the name of Mack J. Fulwyler, entitled "Single Drop Separator"; and U.S. Pat. No. 4,487,320 in the name of Robert E. Auer, entitled "Method And Apparatus For Detecting Change In The Break-Off Point In A Droplet Generation System". The last four of the above noted patents are owned by the assignee hereof.

By appropriate design of the flow chamber, and by knowing the frequency of the ultrasonic or acoustic driver causing the formation of the droplets, it is possible to predict, with relative accuracy, the time that each formed droplet will be completely formed and in a position to be deflected. By placing an appropriate charge on the stream at the instant before a droplet actually breaks away from the stream and, by appropriately positioning the deflection plates at or below that same location, the formed droplet can be caused to be deflected in one of two different directions; in addition, the amount of charge can be varied to cause a greater or lesser deflection. Thus, the technology of the prior art permits the detection and sorting of many specific cells.

A problem with the prior art devices is knowing the precise time at which a cell, which, at a previous time and location had been detected, will be incorporated into one or another droplet. In other words, the problem is not in sorting individual droplets, but rather in determining what droplet to sort. One reason for this problem is that the cells flowing past the detection station flow in a asynchronous manner, that is, the cells being detected can flow into the detection chamber at any instance of time without any correlation to the ultrasonic or acoustic driver frequency causing the formation of the droplets. Thus, a cell, which has been detected, may exist in any one of at least two possible successive droplets or, in some instances, more than two successive possible droplets, depending upon the care taken in designing the flow chamber. Alternatively, the cells being detected may occur too close together, such that insufficient time for detecting exists; even if sufficient processing time is available, more than one particle could end up in a single droplet or under certain circumstances successive droplets could contain a detected and undetected particle.

The prior art has solved the above noted problems of placement of the particle in specific droplets by aborting the sorting process where the cells being sorted were detected too close together. Alternatively, the sorting process could be continued, but the obtained results would lack purity.

Where the successive detected cells are the same, sorting errors can be tolerated more readily without giving up the desired purity of the sorted result. However if the successive cells are different, then much greater care must be taken to assure the purity of the result. No prior art machine takes advantage of this distinction in order to increase sort yields based on a determination of whether successive cells, detected too closely in time, can still be sorted if they are the same type.

SUMMARY OF THE INVENTION

In accordance with one aspect of this invention, there is provided a particle detecting and sorting apparatus having a detection station for asynchronously providing a set of data signals manifesting the detection and various parameters of a particle flowing in a liquid stream containing a plurality of such particles. The apparatus further includes a sorting station having means responsive to a droplet signal for breaking the liquid stream into a series of droplets, only certain ones of which contain the detected particles, and means for sorting the droplets into various categories. The apparatus further has logic means for detecting coincidences of particles at the sorting station comprising means, responsive to the data signals, for providing a series of category signals, in synchronism with the droplet signals and at a rate greater than the rate of the droplet signals. Only one of the category signals can manifest a detected particle at any given time. In addition, the logic means includes means for storing a plurality of successive category signals and means, coupled to the means for storing, for detecting, for each one category signal provided, a coincidence in the occurrence of that one category signal relative to those category signals occurring both before and after the one category signal and for selectively aborting the sorting of a droplet associated with the one category signal having a detected coincidence.

DESCRIPTION OF THE DRAWINGS

By way of example, illustrative embodiments of the invention will now be described with reference to the accompanying drawings, in which.

DETAILED DESCRIPTION

Figure 1:
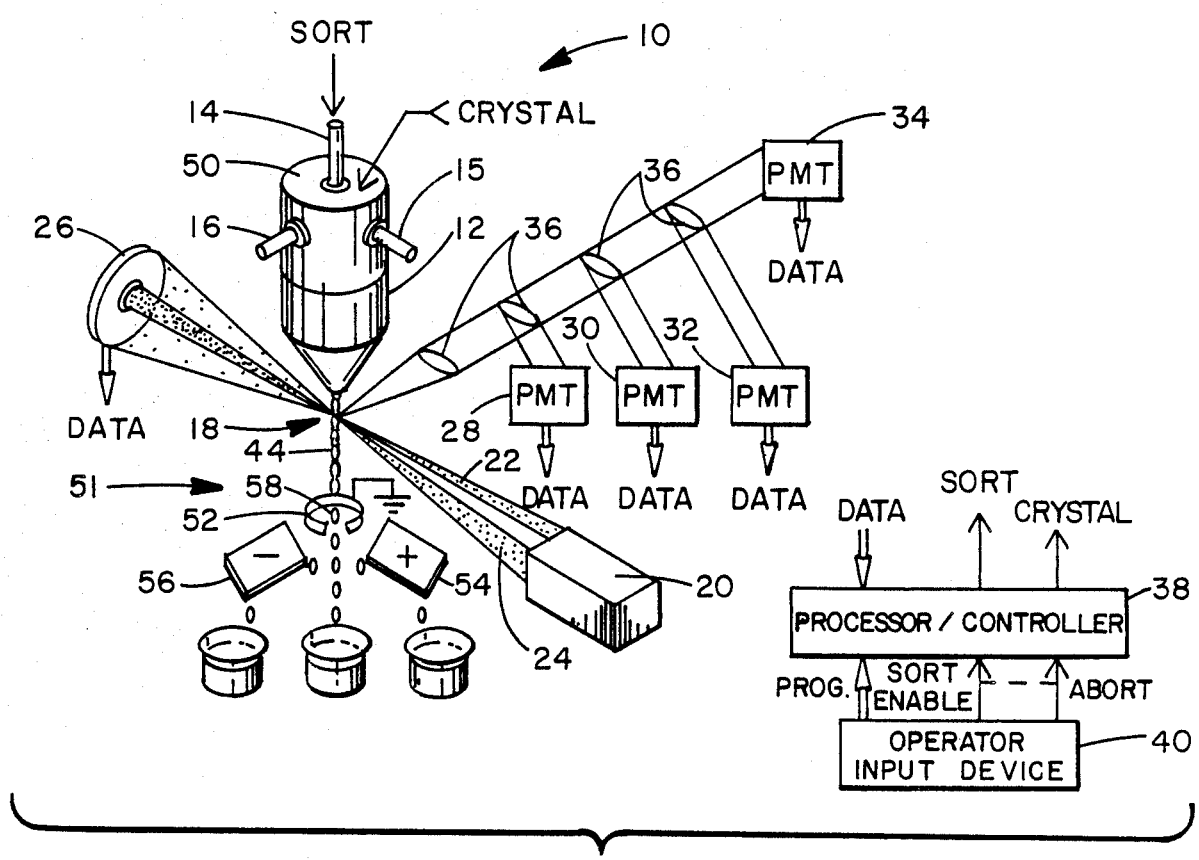
FIG. 1 shows a conventional flow cytometer and sorting system having the improved coincidence arbitration circuit of the subject invention.

Referring now to FIG. 1, a conventional flow cytometry sorting system 10 is shown incorporating the new coincidence arbitration features of the subject invention. Mechanically and optically, this system may be similar to those flow cytometry systems sold under the brand name Epics ® 750, manufactured and sold by the Coulter ® Corporation, of Hialeah, Fla. The key component of system 10 is a flow chamber 12, which includes a sample inlet 14 for receiving a sample containing particles, such as stained blood cells, to be identified, a waste outlet 15 and a sheath inlet 16 for receiving a sheath fluid, such as isotonic saline, sold under the brand name Isoflow ® manufactured and sold by Coulter Corporation of Hialeah, Fla. In addition, flow chamber 12 includes a detection station 18 through which the cells to be identified pass while contained in a narrow jet stream or column of sample fluid surrounded by the sheath fluid. Alternatively, detection station 18 may be a chamber in which the particles are detected prior to being formed into the column.

A laser mechanism 20 directs a pair of laser beams 22 and 24 towards detection station 18. Beam 22 may be an argon laser beam and beam 24 may be a dye beam used specifically to excite molecules on the stained cells, thereby causing fluorescent light to be emitted. Alternatively, a single laser beam could be used for both purposes. Various different type of cells can be detected by measuring the light scattered from the cell, as well as the fluorescent energy generated by the energized dye. The light scatter is detected by a forward angle light scatter photodetector 26 and by a photomultiplier tube (PMT) 28. Photodetector 26 measures the forward scattered light from the back, or dark, side of the cell being detected relative to the laser beams 22 and 24. In addition, photodetector 26 provides a data signal manifesting the amount of forward light scatter from the cell being detected in detector station 18. PMT 28 measures the side light scatter and is positioned at a ninety degree angle with respect to the direction of laser beams 22 and 24. PMT 28 also provides a data signal manifesting the amount of side light scatter. The two light scatter sensors 26 and 28 are useful for collecting information regarding the size, optical density and granularity of the cell being detected and this information is useful for aiding in identifying the particular type of cell.

The fluorescent emission from the detected cell, caused by beam 24 energizing the staining material, is measured by a plurality, such as three, photomultiplier tubes (PMT's) 30, 32, and 34, positioned 90 degrees with respect to the direction of laser beams 22 and 24. Each of the PMT's 30, 32, and 34 provide a data signal manifesting the intensity of a particular wave length, or color, of the emitted fluorescent energy. Appropriate lenses and filter elements 36 are used to direct the side scatter and fluorescent light to the PMT's 28, 30, 32 and 34 in a conventional manner.

The various data signals from detectors 26, 28, 30, 32 and 34 are applied to a processor/controller 38, which also receives signals from an operator input device 40, such as a keyboard or touch actuated display device. Among the signals provided from input device 40 to processor/controller 38 are various programming signals (PROG.) used to program processor/controller 38 based on, for example, the type of cell to be identified or the type of stain placed on the cells. In addition, various signals, such as SORT ENABLE, indicating the device has been turned on may be provided to processor/controller 38 from input device 40, or may be generated internally within processor/controller 38. Lastly, certain operator selectable command signals, such as the ABORT signal, are provided from input device 40 to processor/controller 38. These signals indicate the manner of desired operation by system 10; for example, the provision of the ABORT signal manifests a command to abort the sorting process upon detection of a coincidence situation.

Processor/controller 38 processes the DATA signals in accordance with the signals received from input device 40 to identify and cause the sorting of the detected cells to occur in the manner described hereafter. Upon completion of the processing, processor/controller 38 provides two signals to flow chamber 12, labeled as the SORT signal and the CRYSTAL signal. The purpose of the SORT signal is to indicate whether, and if so how, a particular droplet is to be sorted and the purpose of the CRYSTAL signal is to cause the formation of the droplets, as will be explained hereafter in more detail.

Figure 2:
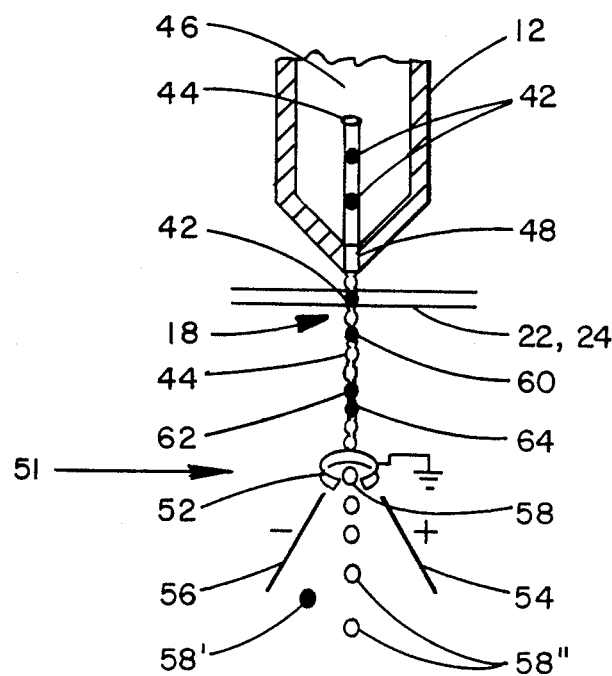
FIG. 2 shows a more detailed view of the formation of the droplets in the system shown in FIG. 1.

Referring now to FIG. 2 in addition to FIG. 1, after a cell 42 is detected at detecting station 18, it continues a downward flow through flow chamber 12 within the cell jet stream column 44. Column 44 is surrounded and maintained centered in flow chamber 12 by a sheath fluid 46 until it reaches the exits opening 48 of flow chamber 12. At the small exit opening 48, the column 44 of cells and sheath fluid 46 are combined under great pressure and exit through flow chamber 12 as a jet stream. The CRYSTAL signal is applied to an ultrasonic wave generator 50 and causes the jet stream 44 of flowing fluid exiting through exit opening 48 to begin forming into droplets based on the frequency of the CRYSTAL signal. As best seen in FIG. 2, it takes many cycles of the crystal signal before an actual droplet breaks loose from column 44. For example, it can require between 18 and 30 droplet periods from the time the stream exits opening 48 for a droplet to be completely free from the jet stream 44, depending upon the frequency and drive level. The actual point where this occurs is measurable and each freed droplet will first exist at substantially the same distance away from exit opening 48 each time.

At, or below, the position the first independent droplet 58 is formed, an almost closed loop electrode 52 is positioned so that the droplet 58 goes through the center of electrode 52. Alternatively, a plate with a slit or hole may be used. This position is known as the sorting station 51. Electrode 52 is placed at electrical ground potential. Below ring electrode 52, a positive deflection plate 54 and a negative deflection plate 56 are provided. The sheath fluid 46 is electrically conductive and the SORT signal may be applied through sample inlet 14 to cause the final undetached droplet being formed along column 44 to be uncharged if no sorting is desired or to be charged positively or negatively, depending on whether a right or left sort is desired. In addition, the amplitude of the charge may vary on whether a far right, near right, far left, or near left sort is desired. As the droplet being formed breaks loose from column 44, it retains the charge defined by the SORT signal and is deflected right or left based upon that charge. An example of such a sorted droplet containing a detected and identified cell is droplet 58'. If the SORT signal is zero and no charge is provided to the droplet being formed, the formed droplet will continue in a straight line due to the exiting pressure, as indicated by droplet 58".

While the distance from exit opening 48 to the point where the first droplet 58 breaks free may be estimated with relative accuracy, several problems exist with respect to the positioning of the various cells 42 in the formed droplets. First, as indicated at the position of cell 60, a cell 60 may exit opening 48 and be positioned between two forming droplets. In this instance, cell 60 may go in either of the two droplets, depending on several factors which are not predictable with sufficient accuracy to determine within which droplet cell 60 will ultimately end up. However, it can only be predicted with sufficient accuracy that cell 60 will end up in one of two particular droplets. This factor becomes of particular concern, when, for example, two cells 62 and 64 could potentially end up in either adjacent droplets as shown, or in the same droplet, because either could have been in a droplet on either side thereof. Thus, it is impossible to accurately predict which droplet is to be sorted. However, if both cells 62 and 64 have been identified as the same type of cell, then a sorting procedure can be still performed because no impurity error will be introduced even if the two cells become combined in the same droplet sorted. Thus, the problem of coincidence, that is the possibility of two cells occupying the same droplet, is only a problem if the two cells 62 and 64 are different. It should be noted that if at detection station 18 the two adjacent cells had been determined to be the same cells, then they both may be sorted along with the droplets on either side thereof and accuracy in the sorting process will be maintained.

Figure 3:
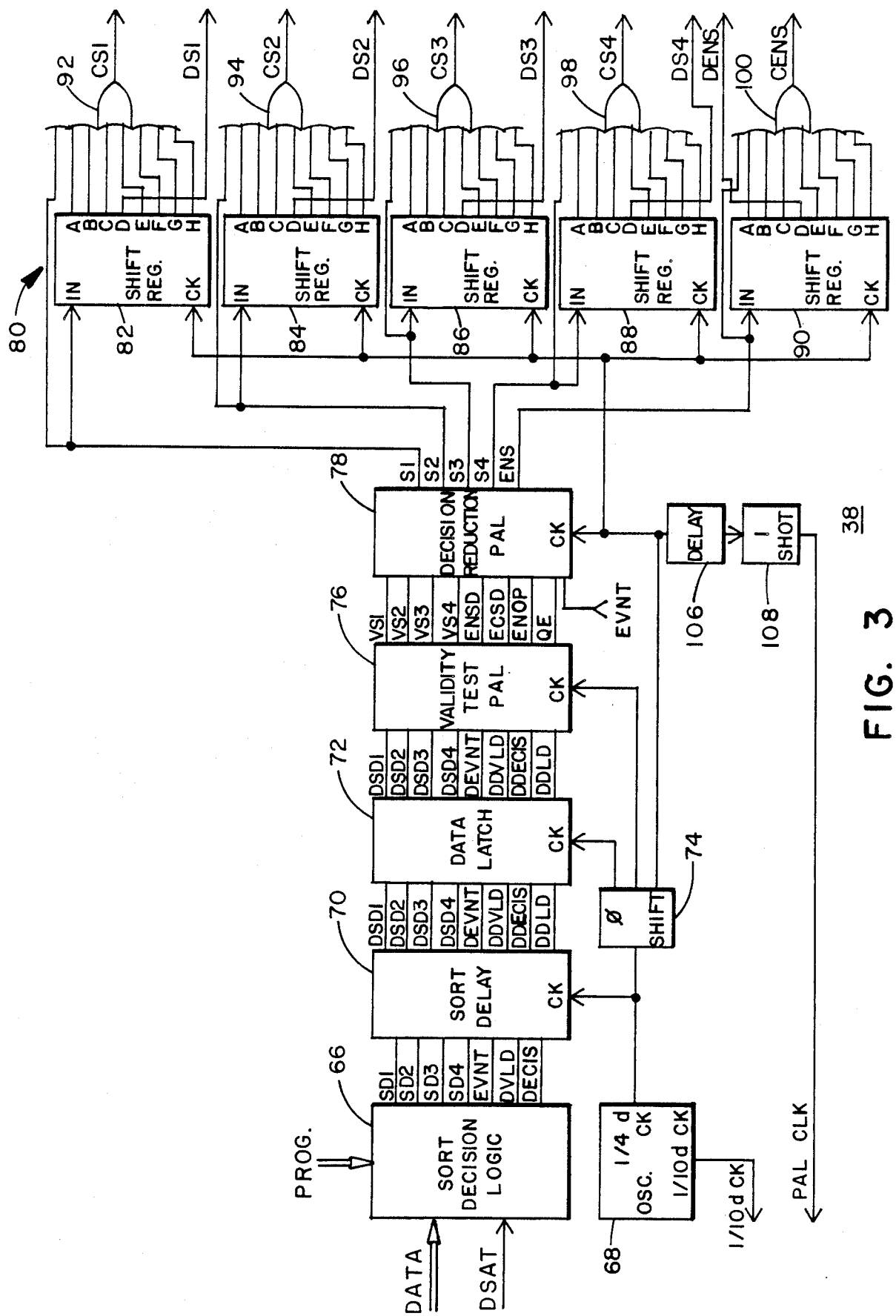
FIG. 3 shows a first portion of the coincidence arbitration circuit of the subject invention.
Figure 4:
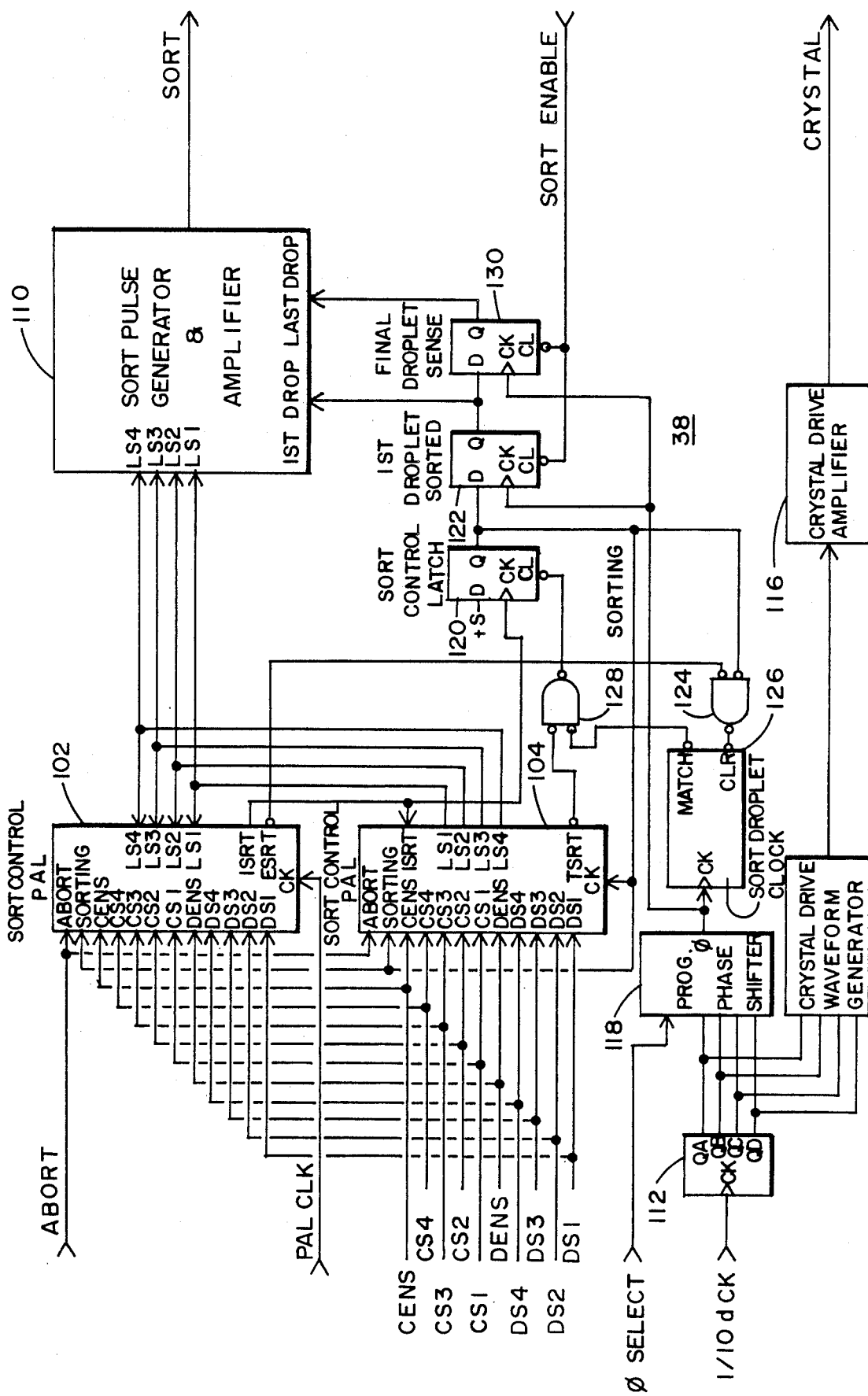
FIG. 4 shows the remainder of the coincidence arbitration circuit of the subject invention.

Referring now to FIGS. 3 and 4, the details of processor/controller 38 will now be described. In processor/controller 38, the entire system is operated based on a clocking frequency related to the frequency of the CRYSTAL signal controlling the rate of formation of the various droplets to occur, such as droplet 58 shown in FIG. 2. A special quarter droplet clocking frequency is also used for detecting potential coincidences of cells in droplets. Signal processing and identifying circuitry (not shown) associated with processor/controller 38 responds to the signals from the various detectors 26, 28, 30, 32 and 34, shown in FIG. 1 and generates a DSAT signal and digitized DATA signals each time a new particle, or other event, is detected. The leading edge of each DSAT signal manifests the detection of a new particle event identifiable by the DATA signals. A quarter droplet cycle time period is generally sufficient to provide the required DSAT and DATA signal information from the various detectors 26, 28, 30, 32 and 34. As will be hereafter described in more detail, one of the principles of the subject invention is to measure one full droplet, or four quarter droplet periods, on each side of each detected cell to determine whether a coincidence of detected cells can occur, that is, whether two cells are in the same or adjacent droplets, such as seen by cell 62 and 64 in FIG. 2.

Referring to FIG. 3 specifically, the DATA and DSAT signals are both applied to sort decision logic 66. Sort decision logic 66 may also be responsive to the programming signals, PROG, from input device 40 for programming sort decision logic 66 with the required information to make the initials decisions of what type of cell has been detected and manifested by the DATA signals. The leading edge of the DSAT signal indicates that a cell, or other detectable event, has occurred identifiable by the DATA signals. Both the DSAT and DATA signals are applied to sort decision logic 40 at an asynchronous rate with respect to the quarter droplet clocking signals, $\frac{1}{4}$ d CK, which may be provided from oscillator 68. In response to the DSAT and DATA signals, sort decision logic 66 provides four sort decision possibilities signals, labeled SD1, SD2, SD3 and SD4. These four signals represent, for example, a far right, near right, near left and far left sorts and anywhere from zero to all four may be made active, depending on the response of sort decision logic to the DATA signal parameters and the programming instructions PROG from the operator. In addition, sort decision logic 66 provides an event signal, EVNT, manifesting the occurrence of an event, such as will be indicated by the provision of a DSAT signal resulting from the detection of a cell 42, or other object, in the path of laser beams 22 and 24 at detection station 18. Further, a DVLD signal is provided manifesting the data is valid, that is a match between an event and a decision has occurred within prescribed time limits. Finally, the sort decision logic 66 provides a DECIS signal, which manifests that a decision is possible, that is, no other DSAT signal were provided during the time that the DATA from the preceding DSAT signal was being processed.

Each of the signals from sort decision logic 66 are provided to sort delay 70, where they are delayed by an amount related to the time it takes for a cell to travel from detection station 18 to sorting station 51 in FIGS. 1 and 2. In practice, the amount of the delay provided by sort delay 70 is approximately one and one quarter droplet times less than the time required for a freed droplet 58 to reach sorting station 51, in order to provide time for the coincidence detection to be completed, as described hereafter. In addition, sort delay 70 is responsive to the quarter droplet clock signal from oscillator 68 for synchronizing the previously asynchronous signals provided thereto. Sort delay 70 provides the delayed and synchronized versions of the signals provided thereto from sort decision logic 66 and, in addition, provides a DDLD signal that manifests a sort decision has been loaded into sort delay 70.

The eight signals from sort delay 70 are provided to data latch 72 which is clocked by a slightly phase shifted quarter droplet signal applied from oscillator 68 through phase shift circuit 74. Because an event manifested by the DSAT signal and its associated DATA signals will typically last for less than a quarter of a droplet time period, the output signals from both sort delay 70 and from data latch 72 will change with each quarter droplet clock signal provided from oscillator 68 and phase shift circuit 74. Thus, each time a new event is detected and a new DSAT signal is provided, a different set of signals will be provided from the output of sort delay 70 and data latch 72. It should be noted at this time that the output signals from sort delay 70 and data latch 72 occur approximately one and one quarter droplet periods prior to the initiation of the SORT pulse signal, as will be described hereafter.

The output signals from data latch 72 are all provided to validity test programmable array logic (PAL) circuit 76. During the quarter droplet time period following the latching of the delayed signals by the data latch 70, the data provided from data latch 70 is tested for validity by validity test PAL 76. The results of the testing, which are latched at the output of the validity test PAL 76, are as follows:

1. Four positive sort decision signals, VS1, VS2, VS3 and VS4, are provided, with one signal for each of the four possible sorting directions and a positive signal for only one of the four possible sorting decisions being possible and then only if all of the validity requirements are met.

2. The ENSD signal manifesting that there was a valid event with a decision that no sort criteria was satisfied and therefore no sort decision was issued. For example, a cell was tested but not programmed to be sorted by the operator.

3. The ECSD signal manifesting that conflicting valid sort decisions was issued.

4. The ENOP signal manifesting that no sort decision was possible and therefore no sort decision was issued.

For example, the system was busy when the DSAT signal was issued.

5. The QE signal manifesting that a questionable event was detected and therefore no sort decision was issued.

The logical equations for validity test PAL 76 are as follows:

| | |
|---|---|
| VS1: | = DSD1 * /DSD2 * /DSD3 * /DSD4 * DEVNT * DDVLD * DDECIS * DDLD |
| VS2: | = DSD1 * DSD2 * /DSD3 * /DSD4 * DEVNT * DDVLD * DDECIS * DDLD |
| VS3: | = /DSL1 * /DSD2 * DSD3 * /DSD4 * DEVNT * DDVLD * DDECIS * DDLD |
| VS4: | = /DSL1 * /DSD2 * /DSD3 * DSD4 * DEVNT * DDVLD * DDECIS * DDLD |
| ENSD: | = /DSD1 * /DSD2 * /DSD3 * /DSD4 * DEVNT * DDVLD * DDECIS * DDLD |
| ECSD: | = DSL1 * DSD2 * DEVNT * DDVLD * DDECIS * DDLD<br>+ DSD1 * DSD3 * DEVNT * DDVLD * DDECIS * DDLD<br>+ DSD1 * DSD4 * DEVNT * DDVLD * DDECIS * DDLD<br>+ DSD2 * DSD3 * DEVNT * DDVLD * DDECIS * DDLD<br>+ DSD2 * DSD4 * DEVNT * DDVLD * DDECIS * DDLD<br>+ DSD3 * DSD4 * DEVNT * DDVLD * DDECIS * DDLD |
| ENDP: | = DEVNT * /DDVLD |
| QE: | = DSD1 * /DEVNT<br>+ DSD2 * /DEVNT<br>+ DSD3 * /DEVNT<br>+ DSD4 * /DEVNT<br>+ DEVNT * /DDVLD * /DDECIS<br>+ DEVNT * DDVLD * DDECIS * /DDLD<br>+ /DEVNT * DDECIS<br>+ /DEVNT * DDLD |

FUNCTION TABLE
/QE DSD1 DSD2 DSD3 DSD4 DEVNT DDVLD DDECIS DDLD
/ENDP /ECSD /ENSD /VS1 /VS2 /VS3 /VS4

| / O E | C K | L S L 1 | L S L 2 | L S R 1 | L S R 2 | L E V N T | L D E V L D S | D E C I D S | L D D L D | / E Q E P | E N C S D D | E E N S D D | / V S 2 | / V S 1 | / V S 2 | / V S 1 |
|---|---|---|---|---|---|---|---|---|---|---|---|---|---|---|---|---|
| L | C | H | L | L | L | H | H | H | H | H | H | H | H | H | H | L |
| L | C | L | H | L | L | H | H | H | H | H | H | H | H | H | L | H |
| L | C | L | L | H | L | H | H | H | H | H | H | H | H | L | H | H |
| L | C | L | L | L | H | H | H | H | H | H | H | H | L | H | H | H |
| L | C | L | L | L | L | H | H | H | H | H | H | L | H | H | H | H |
| L | C | H | H | L | L | H | H | H | H | H | L | H | H | H | H | H |
| L | C | L | L | L | H | L | H | H | H | H | L | H | H | H | H | H |
| L | C | H | L | L | L | L | H | H | H | L | H | H | H | H | H | H |
| L | C | L | L | L | L | H | H | L | H | L | H | H | H | H | H | H |
| L | C | L | L | L | L | H | H | H | L | L | H | H | H | H | H | H |

The various outputs from the validity test PAL are provided to a decision reduction PAL 78, where, in response to the quarter droplet clock signal from phase shift circuit 74, the results are reduced to the four outputs S1, S2, S3 and S4 which manifest a positive sort decisions for each of the four possible directions and a single output, ENS, that manifests a possible event for which no positive sort decision was or could have been made. Again, the output of the decision reduction PAL 78 follows the decisions of the validity test PAL 76 by one quarter of a droplet period. In addition, the decision reduction PAL 78 receives an EVNT signal from a sorting diagnostic system (not shown) which receives the output of the data latch 72 and validity test PAL 76 for performing certain diagnostic functions on processor/controller 38.

The logical equations for decision reduction PAL 78 are as follows:

S1  = EVNT * /QE * /ENDP * /ECSD * /ENSD * VS1 * /VS2

-continued

```
           * /VS3 * /VS4
S2 :    = EVNT * /QE * /ENDP * /ECSD * /ENSD * /VS1 * VS2
           * /VS3 * /VS4
S3 :    = EVNT * /QE * /ENDP * /ECSD * /ENSD * /VS1 * VS2
           * VS3 * /VS4
S4 :    = EVNT * /QE * ENDP * /ECSD * /ENSD * /VS1 * VS2
           * /VS3 * VS4
ENS :   = EVNT * QE
           + EVNT * ENDP
           + EVNT * ECSD
           + EVNT * ENSD
FUNCTION TABLE
/EVNT /QE /ENDP /ECSD /ENSD /VS1 /VS2 /VS3 /VS4 /S1 /S2 /S3
/S4 /ENS
;
;
;          /     /  /  /  /  /  /  /   /  /  /  /  /
;          E     E  E  E  I  I  I  I   O  O  O  O  /
;          V  /  N  C  N  S  S  S  S   S  S  S  S  E
;    O  C  N  O  D  S  S  R  R  L  L   L  L  R  R  N
;    E  K  T  E  P  D  D  2  1  2  1   1  2  1  2  S
     L  C  L  L  H  H  H  H  H  H  H   H  H  H  H  L
     L  C  L  H  L  H  H  H  H  H  H   H  H  H  H  L
     L  C  L  H  H  L  H  H  H  H  H   H  H  H  H  L
     L  C  L  H  H  H  L  H  H  H  H   H  H  H  H  L
     L  C  L  H  H  H  H  H  H  H  L   L  H  H  H  H
     L  C  L  H  H  H  H  H  L  H  H   H  L  H  H  H
     L  C  L  H  H  H  H  L  H  H  H   H  H  L  H  H
     L  C  L  H  H  H  L  H  H  H  H   H  H  H  L  H
     L  C  L  H  H  H  H  H  H  L  L   H  H  H  H  H
     L  C  L  H  H  H  H  H  L  H  L   H  H  H  H  H
```

The five signals S1 through S4 and ENS from the decision reduction PAL 78 are provided to the sort initiation and coincidence detection circuit 80, where a determination of a coincidence of two detected events being in adjacent droplets is made. Circuit 80 includes five eight stage shift registers 82, 84, 86, 88 and 90 each having eight stages with output signals labeled A, B, C, D, E, F, G and H. Each shift register 82, 84, 86, 88 and 90 includes a data input IN having a respective one of the S1, S2, S3, S4 and ENS signals coupled thereto and may be considered as associated with the one of those signals coupled thereto. In addition each shift register 82, 84, 86, 88 and 90 has a clock input CK having coupled thereto the same phase adjusted quarter droplet clock signal coupled to decision reduction PAL 78. Coupled in this manner, the combination of each decision reduction PAL 78 output and its associated shift register 82, 84, 86, 88 and 90 constitutes a delay of nine quarter droplets.

As previously discussed, the time of formation of droplet 58 is predictable; however, an uncertainty exists as to whether a cell detected at detection station 18 is going to be in droplet 58, or one of the droplets on either side of droplet 58. Thus, by looking at the event manifested by the D outputs of shift registers 82, 84, 86, 88 and 90, one can compare every event with those events, if any, occurring during the four proceeding quarter droplet times, as manifested at the decision reduction PAL 78 outputs and the A, B or C shift register 82, 84, 86, 88 and 90 output signals or with those events, if any, occurring during the four succeeding quarter droplet times, as manifested at the E, F, G and H shift register 82, 84, 86, 88 and 90 output signals.

An eight input OR gate 92, 94, 96, 98 and 100 is associated with each shift register 82, 84, 86, 88 and 90 and has coupled thereto the associated one of the outputs of decision reduction PAL 78 and the A, B, C, E, F, G and H outputs from its associated shift register. The output of each one of the OR gates 92, 94, 96, 98 and 100 is a signal labeled as CS1, CS2, CS3, CS4 and CENS and activation of these signals indicates that a positive event has been manifested by one of the inputs, other than the middle (D) output from the shift registers 82, 84, 86, 88 and 90. In other words, one can determine that a cell has been detected at detection station 18 in FIGS. 1 and 2 and that detected cell, by the time in question, has become positioned within one droplet period (four quarter droplet time periods) of being formed into a separate droplet 58.

The output of the D stage of the shift registers 82, 84, 86, 88 and 90 is relabeled as the DS1, DS2, DS3, DS4 and DENS signals. A positive indication by one of these signals manifest the first estimate that a detected cell is included in droplet 58 as it is about to be set free of the column 44. As previously indicated, the actual position of the detected cell would be within one droplet (four quarter droplet time periods) of the first estimate. As will be described in detail hereafter, the DS1, DS2, DS3, DS4 and DENS signals are used to initiate and extend the sorting sequences and the CS1, CS2, CS3, CS4 and CENS are used to detect for possible coincidences. Because of the previous processing in the validity test PAL 76 and the decision reduction PAL 78, it should be impossible for two or more of the DS1, DS2, DS3, DS4 and DENS signals to manifest a positive event at the same time.

Referring now to FIG. 4, the actual detection and response to a coincidence is performed by a first sort control PAL circuit 102 and a second sort control PAL circuit 104. Alternatively, a single larger PAL could have been used. Each of the PAL circuits 102 and 104 have the DS1, DS2, DS3, DS4, DENS, CS1, CS2, CS3, CS4 and CENS signals from sort initiation and coincidence detection circuit 80 applied to inputs thereof. In addition, the ABORT command from input device 40 is provided to indicate whether the operator desires a sort or abort to occur upon the detection of a coincidence. For example, if a rare cell is being detected, it may be desirable to get all of the cells and the ABORT command will be off. On the other hand, if purity is desired, the ABORT command will be on. In addition, a signal, labeled SORTING, is provided to both PAL circuits 102 and 104 and manifests that droplet 58 is being sorted in response to a SORT pulse being generated.

Both PAL circuits 102 and 104 are clocked by the PAL CLK signal. This signal is provided from FIG. 3 by providing the phase adjusted quarter droplet clock signal applied to decision reduction PAL 78 through a delay circuit 106 and monostable multivibrator, or one shot, circuit 108. These two circuits provide a signal to the two PAL circuits 102 and 104 sufficiently delayed and of sufficient duration to permit the calculations performed thereby to occur.

In addition to the above noted common signals provided to the two PAL circuits 102 and 104, PAL circuit 102 provides the ISRT signal, which manifests a sort initiate command, and the ESRT signal, which manifests that a previous sort command is being extended. The ISRT signal from PAL circuit 102 is provided as an input to PAL circuit 104, which in response thereto causes the LS1, LS2, LS3 and LS4 sort direction command signals to be provided back to PAL circuit 102 to be used in generating the extended sort command ESRT signal. In addition, the LS1, LS2, LS3 and LS4 sort direction command signals are applied to sort pulse generator and amplifier circuit 110, for use therein to generate the SORT signal. Lastly, PAL circuit 104 provides the TSRT signal, which is a command to terminate the provision of the SORT signal after the equations are satisfied.

The logical equations for the PAL circuit 102 are as follows:

```
ISRT   = CK * /ABORT * /SORTING * DS1 * /DS2 * /DS3 * /DS4
       + CK * /ABORT * /SORTING * /DS1 * DS2 * /DS3 * DS4
       + CK * /ABORT * /SORTING * /DS1 * /DS2 * DS3 * /DS4
       + CK * /ABORT * /SORTING * /DS1 * /DS2 * /DS3 * DS4
       + CK * ABORT * /SORTING * DS1 * /DS2 * /DS3 * /DS4 *
         /CS2 * /CS3 * /CS4 * /CENS
       + CK * ABORT * /SORTING * /DS1 * DS2 * /DS3 * DS4 *
         /CS1 * /CS3 * /CS4 * CENS
       + CK * ABORT * /SORTING * /DS1 * /DS2 * DS3 * /DS4 *
         /CS1 * /CS2 * /CS4 * /CENS
       + CK * ABORT * /SORTING * /DS1 * /DS2 * /DS3 * DS4 *
         /CS1 * /CS2 * /CS3 * /CENS
ESRT   = CK * /ABORT * SORTING * LS1 * DS1 * /DS2 * /DS3 * /DS4
       + CK * /ABORT * SORTING * LS2 * /DS1 * DS2 * /DS3 * /DS4
       + CK * /ABORT * SORTING * LS3 * /DS1 * /DS2 * DS3 * /DS4
       + CK * /ABORT * SORTING * LS4 * /DS1 * /DS2 * /DS3 * DS4
         * LS1 * DS1 * /DS2 * /DS3
       + CK * ABORT * SORTING * LS1 * /DS1 * DS2 * /DS3 * /DS4
         * /CS2 * /CS3 * /CS4 * /CENS
       + CK * ABORT * SORTING * LS2 * /DS1 * DS2 * /DS3 * /DS4
         * /CS1 * /CS3 * /CS4 * /CENS
       + CK * ABORT * SORTING * LS3 * /DS1 * /DS2 * DS3 * /DS4
         * /CS1 * /CS2 * /CS4 * /CENS
       + CK * ABORT * SORTING * LS4 * /DS1 * /DS2 * /DS3 * DS4
         * /CS1 * /CS2 * /CS3 * /CENS
```

FUNCTION TABLE
CK ABORT SORTING CENS CS4 CS3 CS2 CS1 /DENS /DS4 /DS3 /DS2 /DS1 /LS2 /LS1 /LS4 /LS3 /ESRT /ISRT

```
;      A    S
;      B    O
;      C    R                    /  /  /  /  /              /  /
;      L    R    T  C  C  C  C  C  D  D  D  D  /  /  /  /              E  I
;      K    T    I  N  N  S  S  S  N  S  S  S  S  S  S  S  N  N  N  S  S
;      1    O    N  S  R  R  L  S  R  R  L  L  L  L  R  R  C  C  C  R  R
;      N    N    G  E  2  1  2  1  E  2  1  2  1  2  1  1  2  3  T  T
       C    L    H  L  L  L  L  L  H  H  H  H  H  H  H  H  H  H  H  H  H
```

The logical equations for the PAL circuit 102 are as follows:

```
TSRT   = SUB1 + SUB2
       + DS1 * ABORT * /SORTING * /ISRT
       + DS2 * ABORT * /SORTING * /ISRT
       + DS3 * ABORT * /SORTING * /ISRT
       + DS4 * ABORT * /SORTING * /ISRT
SUB1   = ABORT * SORTING * LS1 * CS2
       + ABORT * SORTING * LS1 * CS3
       + ABORT * SORTING * LS1 * CS4
       + ABORT * SORTING * LS2 * CS1
       + ABORT * SORTING * LS2 * CS3
       + ABORT * SORTING * LS2 * CS4
       + ABORT * SORTING * DENS
SUB2   = ABORT * SORTING * LS3 * CS1
       + ABORT * SORTING * LS3 * CS2
       + ABORT * SORTING * LS3 * CS4
       + ABORT * SORTING * LS4 * CS1
       + ABORT * SORTING * LS4 * CS2
       + ABORT * SORTING * LS4 * CS3
       + ABORT * SORTING * CENS
LS1    = DS1 * /ABORT * /DS2 * /DS3 * /DS4
       + DS1 * ABORT * /DS2 /DS3 * DS4
         * /CS2 * /CS3 * /CS4 * /DENS * CENS
LS2    = DS2 * /ABORT * /DS1 * /DS3 * /DS4
       + DS2 * ABORT * /DS1 * /DS3 * /DS4
```

```
           * /CS1 * /CS3 * /CS4 * /DENS * /CENS
   LS3     = DS3 * /ABORT * /DS1 * /DS2 * DS4
           + DS3 * ABORT * /DS1 * /DS2 * /DS4
           * /CS1 * CS2 * /CS4 * /DENS * /CENS
   LS4     = DS4 * /ABORT * /DS1 * /DS2 * /DS3
           + DS4 * ABORT * /DS1 * /DS2 * /DS3
           * /CS1 * /CS2 * /CS3 * /DENS * /CENS
   FUNCTION TABLE:
   ABORT SORTING CENS CS4 CS3 CS2 CS1 /DENS /DS4 /DS3 /DS2
   /DS1 /ISRT /TSRT /SUB2 /LS1 /LS2 /LS3 /LS4 /SUB1
   ;              A   S
   ;              B   O
   ;              O   R                   /   /   /   /   /   /   /   /                           /
   ;              R   T   C   C   C   C   D   D   D   D   I   T   S   /   /   /   /           S
   ;         /    T   I   N   S   S   S   S   N   S   S   S   S   S   U   S   S   S   S       U
   ;    C    O   O   N   S   R   R   L   L   S   R   R   L   L   R   B   L   L   R   R       B
   ;    K    E   N   G   E   2   1   2   1   E   2   1   2   1   T   1   2   1   2   1       1
          C  L   H   H   L   L   L   L   L   H   H   H   H   H   H   H   H   H   H   H       H
```

The one tenth droplet clock signal from oscillator 68 in FIG. 3 is provided to a decade counter 112 in FIG. 4, the outputs of which are provided to crystal drive waveform generator 114. After ten pulses have been provided to decade counter 112, a single pulse is provided from generator 114 and amplified by crystal drive amplifier 116. The output of amplifier 116 is the CRYSTAL signal provided to the ultrasonic generator 50 in flow chamber 12 for causing the formation of the droplets 58, as seen in FIGS. 1 and 2. The droplet frequency is also used to provide the SORT signals from sort pulse generator and amplifier 110, but the signal must be phase adjusted to assure the SORT voltage is provided before the actual formation of the droplet 58. This is accomplished by the programmable phase shifter circuit 118, which responds to a Φ SELECT signal determined during a calibration procedure. The output of programmable phase shifter circuit 118, thus, becomes the clocking signal for providing the SORT signal.

As seen from the logic equations for PAL circuit 102, the ISRT initiate sort command signal is provided by PAL circuit 102 if during the clock period, the system is not already sorting and; if the ABORT signal is disabled, that is, the abort on coincidence detection function is not desired, a positive sort decision is detected in only one of the middle (D) outputs from shift registers 82, 84, 86, 88 or 90; or, if ABORT is enabled, that is the abort on coincidence detection function is desired, a positive sort decision is detected in only one of the middle (D) outputs from shift registers 82, 84, 86, 88 or 90 and no positive event is present in any of the other outputs from shift registers 82, 84, 86, 88 or 90 or decision reduction PAL 78.

The ISRT signal is provided to set the sort control latch 120, thereby causing the SORTING signal provided from the Q output thereof to become high (logic "1"). The SORTING signal is provided back to as data to PAL circuits 102 and 104 and also is used to clock the logical calculations of PAL circuit 104. In addition, the SORTING signal is provided to the data (D) input of a first droplet sorted latch 122 and to one input of AND gate 124. The other input to AND gate 124 is the normally high extended sort ESRT signal from PAL circuit 102. Thus, a normally low (logic "0") signal is provided from the output of AND gate 124 to the CLR input of a sort droplet clock circuit 126. In this condition, each time a droplet clock pulse is provided from phase shifter 118 to the C input of sort droplet clock circuit 126, the MATCH output goes from high to low. The MATCH output from sort droplet clock circuit 126 is provided to one input of AND gate 128, the other input of which receives the normally high TSRT signal from PAL circuit 104. When the Match output from sort droplet clock circuit 126 goes low, it causes the output of AND gate 128 to go low and thereby clears the sort control latch 120.

The droplet clock signal from phase shifter 118 is also applied to the clock inputs of first droplet sorted latch 122 and a final droplet sense latch 130. Both latches 122 and 130 are cleared initially by the SORT ENABLE signal provided at power on from either input device 40 or internally within processor/controller 38. When the CK input of first droplet sorted latch 122 becomes high, the data at the D input is clocked to the Q output and applied to the D input of final droplet sense latch 130 and to the 1st Drop input of the SORT pulse generator and amplifier circuit 110. The sort pulse generator and amplifier circuit 110 responds to the latch 122 signal by initiating the leading edge if the SORT pulse. It should be noted that if a TSRT terminate sort command is issued by PAL circuit 104 prior to the transfer of the sort command from sort control latch 120 to first droplet sense latch 122, no sort process will be initiated because AND gate 128 clears sort control latch 120.

The exact process beyond this point is dependent upon the number of droplets contained in a single sort sequence. If only a single droplet is to be sorted, then sort control latch 120 is cleared after the first droplet sorted latch 122 is set. If more than one successive droplet is to be sorted, the ESRT signal from PAL circuit 102 becomes low, thereby indicating an extended sort, and thus forcing AND gate 124 to clear the sort droplet clock 126 and prevent further pulses therefrom through AND gate 128 to reset sort control latch 120. This situation continues until the ESRT signal again returns to the high level, thereby indication that the extended sort period is completed. With the second droplet timing pulse from phase shifter clock 118, final droplet sense latch 130 is set.

Figure 5:
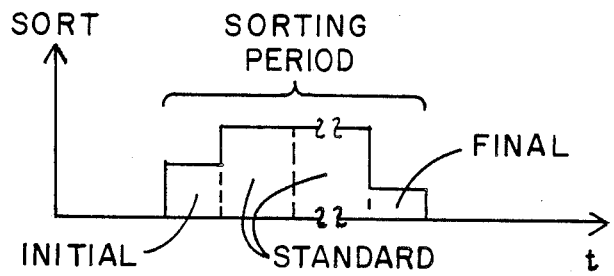
FIG. 5 shows the SORT signal for sorting successive droplets.

As long as the first droplet sorted latch 122 and final droplet sense latch 130 are both set, sort pulse generator and amplifier 110 produces standard sort pulses for each droplet. After the first droplet sorted latch 122 is cleared, leaving only the last droplet sense latch 130 set, sort pulse generator and amplifier produces a terminating sort pulse. The difference between initial, standard and terminating sort pulses are in amplitude and polarity due to the well known differing charge characteristics of the column jet. An example of a SORT pulse having an initial, standard and final amplitude is shown in FIG. 5.

The ESRT extended sort command is generated if during the PAL circuit 102 clock period, it is determined that a SORT pulse is being provided (SORTING is active) and; if ABORT is disabled, a positive sort decision is detected in the D output of the shift registers 82, 84, 86, 88 and 90 that is the same as the current sort direction or; if ABORT is enabled, a positive sort decision is detected only in the D output of the shift registers 82, 84, 86, 88 and 90 that is the same as the current sort direction and a positive event is not present in any of the other outputs of shift registers 82, 84, 86, 88 and 90 or decision reduction PAL 78. The terminate sort command TSRT is generated (rendered low) if ABORT is enabled, the SORTING signal is high and, if an event is detected in any output of shift registers 82, 84, 86, 88 and 90 or decision reduction PAL 78 of a differing sorting direction from that currently taking place. The TSRT signal clears the sort control latch 120, thereby resulting in a normal SORT pulse termination sequence.

Figure 6:
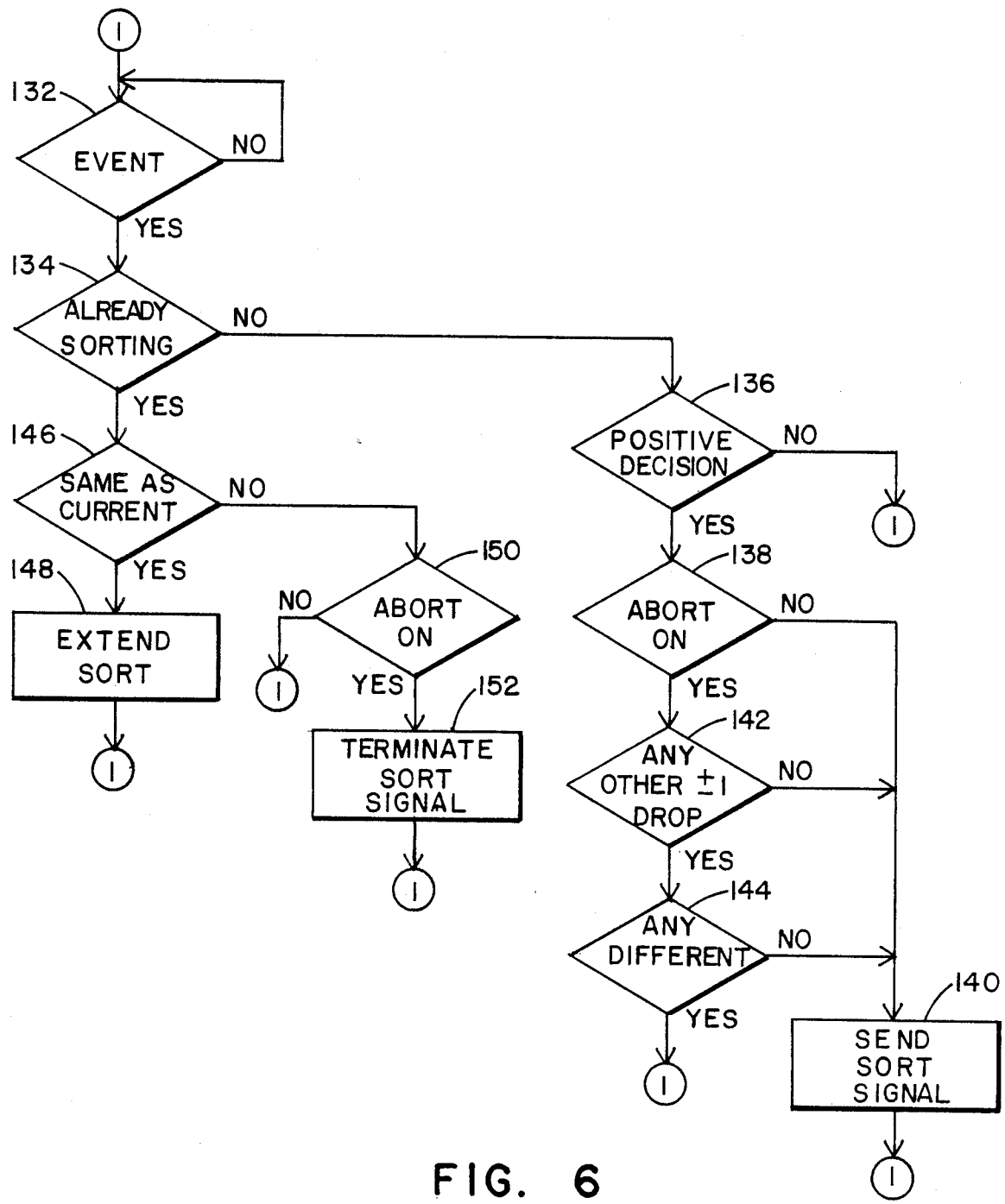
FIG. 6 is a flow diagram useful in understanding the functional aspects of the operation of the coincidence logic of the subject invention.

Referring now to FIG. 6, a flow diagram of the decision logic of the sort control PAL circuits 102 and 104 is shown. First, as indicated by block 132, a determination is made of whether an evenT is occurring. This determination continues until an event is detected. Next, according to block 134, a determination is made of whether the system 10 is already sorting a pulse, that is whether the SORTING signal is provided. If system 10 is not already sorting, then according to block 136, a decision is made whether the event detected is positive. This may be tested by seeing if the DENS and one of the DS1, DS2, DS3 or DS4 signals is provided. If there is no positive decision, then a return to block 122 is indicated.

Next, according to block 138, a determination is made whether the ABORT command is provided; if not, then according to block 140, the SORT pulse is provided by provided the ISRT signal from PAL circuit 102. If the ABORT command were determined to be on at block 138, then according to block 142, a determination is made whether any other events are occurring within one droplet time of the CS1, CS2, CS3, CS4 and CENS signals. If not, then according to block 140, the SORT pulse is provided. If there is a coincidence detected at block 142, then at block 144, a determination is made whether the coincidence requires the same sort, or a different sort. If the same sort is required, then block 140 indicates that the SORT pulse will be provided. If at block 144, it was determined that a different type of sort were required, then no SORT pulse should be provided and a return to block 132 is indicated.

If at block 134, it were determined that system 10 were already sorting a droplet, then, according to block 146, a determination is made whether the droplet being sorted and the new detected event required the same action. If so, then block 148 indicates the extend sort ESRT is provided and the SORT signal is continued. If the new event is different than the event being sorted, then, as indicated by block 150, a determination is made whether the ABORT command is on. If not, a return to block 132 occurs. If the ABORT command is on, then according to block 152, the terminate sort command TSRT is issued and a return to block 132 occurs.

Because of the above described action, system 10 is able to maximize the number of cells captured while maintaining sufficient dead band so as to maintain sorted cell purity.

What is claimed is:

1. A particle detecting and sorting apparatus comprising:
    means for detecting particles in a flowing liquid containing particles, for identifying selected ones of said detected particles and for thereafter forming said flowing liquid into droplets at a droplet formation rate, the time between formed droplets thereby being a droplet formation period, only some of said droplets containing said detected particles;
    means, including delay means, responsive to said detected particles, for providing a sort signal each time a particle is detected, unless a coincidence occurs between that detected particle and one of a non-selected or differently identified detected particle within one droplet formation period of that detected particle; and
    means, responsive to said sort signal, for sorting said droplets.

2. The invention according to claim 1:
    wherein said particles are detected asynchronously and an event signal, manifesting one of the identity or non-identity of each particle is provided each time a particle is detected; and
    wherein said delay means further includes means for synchronizing said event signals with said droplet formation rate.

3. The invention according to claim 2 wherein said means for synchronizing synchronizes each event signal with a clock frequency which is an integral multiple of said droplet formation rate.

4. The invention according to claim 3 wherein said means for providing further includes means for storing a plurality of successive event signals and means for comparing one of said stored event signals with others of said stored event signals occurring both before and after said one event signal.

5. The invention according to claim 4 wherein said sort signal is provided whenever said one stored event signal manifests a detected particle unless said other stored event signals manifest a non-selected particle.

6. The invention according to claim 4 wherein said sort signal is provided whenever said one stored event signal manifests a detected particle unless said other stored event signals manifest a differently identified detected particle.

7. The invention according to claim 6 wherein said sort signal is provided for more than one droplet formation period whenever said one stored event signal and another stored event signal manifests the same detected particle.

8. The invention according to claim 2 wherein said means for providing further includes means for storing a plurality of successive event signals, each event signal being provided in response to the detection of a particle and each event signal manifesting one of the identity or non-identity of each detected particle, and means for comparing one of said stored event signals with others of said stored event signals occurring both before and after said one event signal.

9. The invention according to claim 8 wherein said sort signal is provided whenever said one stored event signal manifests one identity of a detected particle unless said other stored event signals manifest a different identity of a detected particle.

10. The invention according to claim 8 wherein said sort signal is provided for more than one droplet formation period whenever said one stored event signal and another stored event signal manifests the same identity of a detected particle.

11. The invention according to claim 8 wherein said means for storing includes shift registers means having an input, to which said event signal is applied, and a plurality of outputs, each manifesting a successively delayed version of said event signal.

12. The invention according to claim 11 wherein said particles are detected asynchronously and said delay means includes means, responsive to a clock signal, for synchronizing said event signals with said droplet formation rate, said shift register means being clocked by said clock signal to cause said successively delayed version of said event signal.

13. The invention according to claim 12 wherein said delay means is selected to cause each event signal to be manifested at a preselected internal output of said shift register means at the time a droplet is formed containing the identified particle manifested by said shift register means preselected output signal.

14. The invention according to claim 13 wherein said means for comparing includes OR gating means and logic means, said event signal and the non-preselected outputs of said shift register means being coupled to said OR gating means, and said preselected output and said OR gating means output being applied to said logic means.

15. The invention according to claim 14 wherein said logic means provides said sort signal whenever said preselected shift register means output manifests one identity of a detected particle, unless said OR gating means output manifests a different identity of a detected particle.

16. The invention according to claim 15 wherein said logic means provides said sort signal for more than one droplet formation period whenever said preselected shift register means output and said OR gating means output manifest the same identity of a detected particle.

17. The invention according to claim 14 wherein said logic means provides said sort signal for more than one droplet formation period whenever said preselected shift register means output and said OR gating means output manifest the same identity of a detected particle.

18. The invention according to claim 8 wherein said means for storing includes one shift register associated with each event signal manifesting a different identified particle and one shift register associated with the event signal manifesting a non-identified particle, each shift register having an input, to which the associated event signal is applied, and a plurality of outputs, each manifesting a successively delayed version of the applied associated event signal.

19. The invention according to claim 18 wherein said delay means includes means, responsive to a clock signal, for synchronizing said event signals with a said droplet formation rate, each of said shift registers being clocked by said clock signal to cause said successively delayed version of the applied associated event signal.

20. The invention according to claim 19 wherein said delay means is selected to cause each event signal to be manifested at one preselected internal output of an associated shift register at the time a droplet is formed containing the identified particle associated with that shift register.

21. The invention according to claim 20 wherein said means for comparing includes an OR gate associated with each shift register and common logic means, an associated event signal and the non-preselected outputs of each shift register being coupled to the associated OR gate and said preselected outputs, and said OR gates output being applied to said common logic means.

22. The invention according to claim 21 wherein said common logic means provides said sort signal whenever one preselected shift register output manifests one identity of a detected particle, unless said OR gates output manifest a different identity of a detected particle.

23. The invention according to claim 22 wherein said common logic means provides said sort signal for more than one droplet formation period whenever one shift register preselected output and the output of said OR gate associated with that one shift register manifest the same identity of a detected particle.

24. The invention according to claim 21 wherein said common logic means provides said sort signal for more than one droplet formation period whenever one shift register preselected output and the output of said OR gate associated with that one shift register manifest the same identity of a detected particle.

25. A particle detecting and sorting apparatus having a detection station for asynchronously providing a set of data signals manifesting the detection and various parameters of a plurality of particles flowing in a liquid stream containing said plurality of particles, and a sorting station having means, responsive to a droplet signal having a certain droplet rate, for breaking said liquid stream into a series of droplets, only certain ones of which contain said detected particles and means for sorting said droplets into various categories, said apparatus further having logic means for detecting coincidences of particles at said sorting station comprising:
   means, responsive to said data signals, for providing a series of category signals, in synchronism with said droplet signal and at a rate greater than said certain droplet rate, only one of said category signals manifesting a detected particle at any given time;
   means for storing a plurality of successive category signals; and
   means, coupled to said means for storing, for detecting, for each one category signal provided, a coincidence between said one category signal and those category signals occurring within a finite time before and after said one category signal and for selectively aborting the sorting of a droplet associated with said one category signal having a detected coincidence.

26. The invention according to claim 25 wherein said means for storing is a data shifting means having each category signal clocked therein at said greater rate.

27. The invention according to claim 26:
   wherein said data shifting means includes a plurality of stages; and
   wherein said means for detecting compares the data stored in an internal stage of said data shifting means with the data stored by selected ones of the remaining stages of said data shifting means.

28. The invention according to claim 27 wherein said data shifting means is a shift register.

29. The invention according to claim 25 wherein said means for providing includes delay means for delaying the provision of said category signals by an amount related to the time for a particle to travel from said detection station to said sorting station.

30. The invention according to claim 29 wherein delay means has said asynchronous data provided thereto and provides data synchronized with said droplet signal.

31. The invention according to claim 30 wherein said delay means provides said category signals prior to the time a particle is to be sorted at said sorting station.

32. The invention according to claim 29 wherein said delay means provides said category signals prior to the time a particle is to be sorted at said sorting station.

33. The invention according to claim 32 wherein said means for providing further includes means for processing said data to provide said category signals.

34. The invention according to claim 29 wherein said means for providing further includes means for processing said data to provide said category signals.

35. The invention according to claim 25 wherein said means for providing includes means for processing said data to provide said category signals.

36. The invention according to claim 35:
 wherein each set of said data signals include an event signal manifesting the detection of a particle and at least one parameter signal manifesting information about a parameter of that particle manifested by said event signal; and
 wherein said means for processing includes means for accepting said data signals and means for providing a valid event signal and one of a plurality of possible category signals in response to each accepted set of data signals.

37. The invention according to claim 36 wherein said means for processing includes delay means for delaying the provision of said valid event signal and said one category signal by an amount related to the time for a particle to travel from said detection station to said sorting station.

38. The invention according to claim 37 wherein said delay means provides said category signals prior to the time a particle is to be sorted at said sorting station.

39. A method of detecting and sorting a plurality of different particles flowing in a liquid stream, comprising the steps of:
 detecting each particle in said stream and providing a series of asynchronously occurring particle signals manifesting the detection of unidentified particles and a plurality of identified particles;
 forming said stream into a series of sortable droplets in response to a sort signal, selected ones of said droplets containing said particles;
 delaying and synchronizing said particle signals to the formation of said droplets;
 detecting the occurrence of coincidences between said particle signals within a certain time period surrounding the formation of each droplet and whether or not said coincidence is between the same identified particles; and
 providing said sort signal each time said particle signal manifests an identified particle, unless a coincidence with a different identified, or an unidentified, particle is detected.

40. The method according to claim 39 wherein said step of delaying and synchronizing delays said particle signals by an amount of time related to the time between the detection of a particle and the formation of said droplets.

41. The method according to claim 40 wherein said step of detecting includes providing said particle signals through a plurality of shift registers, one for each of said detected identified and unidentified particles and comparing the signal at a center output of each shift register with signals from the remaining outputs of said shift registers for detecting said coincidence.

42. The method according to claim 39 wherein said step of detecting includes providing said particle signals through a plurality of shift registers, each having a plurality of outputs, a shift register being provided for each of said detected identified particles and a shift register being provided for the unidentified particles, and comparing the signal at a center output of each shift register with signals from the remaining outputs of said shift registers for detecting said coincidence.

43. The method according to claim 42 wherein said step of delaying causes said signal at each center output to be provided at the time a droplet is formed.

44. The method according to claim 43 wherein said step of providing said sort signal provides said sort signal for an extended time whenever a coincidence with the same identified particle is detected.

45. The method according to claim 39 wherein said step of providing said sort signal provides said sort signal for an extended time whenever a coincidence with the same identified particle is detected.

* * * * *